(12) United States Patent
Tschida (10) Patent No.: US 7,302,036 B2
(45) Date of Patent: Nov. 27, 2007

(54) SYSTEMS AND METHODS FOR NON-INTRUSIVE INSPECTIONS OF HIGH-VOLTAGE CIRCUIT BREAKERS

(75) Inventor: Dennis Michael Tschida, Molino, FL (US)

(73) Assignee: General Electrical Company, Schenectady, NY (US)

( * ) Notice: Subject to any disclaimer, the term of this patent is extended or adjusted under 35 U.S.C. 154(b) by 56 days.

(21) Appl. No.: 11/164,905

(22) Filed: Dec. 9, 2005

(65) Prior Publication Data
US 2007/0133745 A1 Jun. 14, 2007

(51) Int. Cl.
*G01B 15/06* (2006.01)

(52) U.S. Cl. .......................................... 378/58; 378/57

(58) Field of Classification Search ................... 378/57, 378/58, 54, 62
See application file for complete search history.

(56) References Cited

U.S. PATENT DOCUMENTS 5,286,933 A * 2/1994 Pham .......................... 218/119

FOREIGN PATENT DOCUMENTS

JP           2004-77203 A  *  3/2004

* cited by examiner

*Primary Examiner*—Hoon Song
(74) *Attorney, Agent, or Firm*—Sutherland Asbill & Brennan (57) ABSTRACT

Systems and methods are disclosed for non-intrusively inspecting circuit breakers, which may include one or more connector assemblies. An X-ray unit may be placed at a first location around the circuit breaker while at least one digital imaging plate may be placed at a second location around the circuit breaker. The X-ray unit may generate X-rays, where at least a portion of the generated X-rays traverse a plane that includes at least a portion of the connector assembly and at least a portion of the at least one digital imaging plate. The image that includes at least a portion of the connector assembly may be retrieved from the digital imaging plate and inspected to determine a status of the circuit breaker.

20 Claims, 7 Drawing Sheets

SYSTEMS AND METHODS FOR NON-INTRUSIVE INSPECTIONS OF HIGH-VOLTAGE CIRCUIT BREAKERS

BACKGROUND OF THE INVENTION

1. Field of the Invention

Aspects of the present invention relate generally to circuit breakers, and more particularly, to systems and methods for non-intrusive inspections of high-voltage circuit breakers.

2. Description of the Related Art

High-voltage circuit breakers play an important protective role for high power machinery. Over time, however, these circuit breakers may wear down or experience other malfunctions and problems such as internal arcing. Therefore, these high-voltage circuit breakers must be routinely inspected for problems.

Traditionally, the inspection process has been costly and disruptive to customers. In order to inspect the internal components of the circuit breakers, they must be disassembled. During this disassembly process, the gases utilized internally in the circuit breaker to control arcing, such as sulphur hexafluoride gas, must be carefully contained because they are typically environmentally unsafe. Upon completion of the inspection process, the circuit breaker is reassembled and refilled with gas. However, during the gas refill process, the purity of the gas may oftentimes be compromised, therefore reducing the operational reliability of the circuit breaker. Indeed, experience has shown that the disassembly and reassembly of circuit breakers may reduce their overall operational reliability.

Thus, such an inspection process described above is deemed to be costly and disruptive to customers. Accordingly, there is a need in the industry for non-intrusive inspections of circuit breakers that are less costly and less disruptive than traditional methods.

BRIEF DESCRIPTION OF THE INVENTION

Radiography equipment may be utilized to inspect circuit breakers at a customer site. The use of the radiography equipment allows inspections of these circuit breakers to be performed at a customer site without requiring the disassembly and reassembly of circuit breakers. Instead, the circuit breaker may be inspected by examining images of the internal components obtained through the radiography equipment.

According to one embodiment of the invention, there is method for non-intrusively inspecting circuit breakers. The method includes receiving at least one circuit breaker, where the circuit breaker includes a tank having an interior with one or more connector assemblies, placing an X-ray unit at a first location of an exterior of the tank, and placing at least one digital imaging plate at a second location of the exterior the tank. The method further includes generating X-rays from the X-ray unit, such that at least a portion of the generated X-rays traverse a plane that includes at least a portion of the connector assembly and at least a portion of the at least one digital imaging plate, and retrieving an image from each digital imaging plate, wherein each image includes at least a portion of the connector assembly.

According to an aspect of the invention, the at least one circuit breaker may be positioned at a customer location. According to another aspect of the invention, the method may further include inspecting the image for determining a status of the at least one circuit breaker. The connector assembly may include one or both of a stationary side contact and a moving side contact, and a template may be overlayed over the image of the stationary side contact for determining wear of the stationary side contact. According to another aspect of the invention, retrieving an image may include retrieving an image from each digital imaging plate via at least one scanner unit operable with the digital imaging plate. The image may be directly manipulated on a computer.

According to another embodiment of the invention, there is a system for non-intrusive inspections of circuit breakers. The system includes a circuit breaker having at least one connector assembly, an X-ray unit at a first position of the circuit breaker for transmitting X-ray energy, where the transmitted X-ray energy is directed towards at least a portion of the at least one connector assembly, a digital imaging plate at a second position of the circuit breaker substantially opposite the first position for receiving the transmitted X-ray energy, where the digital imaging plate stores an image that is defined, at least in part, by the received X-ray energy, and a scanner unit in communication with a computer for retrieving the stored image from the digital imaging plate.

According to an aspect of the invention, the stored image captures at least a portion of the at least one connector assembly. The portion of the at least one connector assembly may include a stationary side contact. According to another aspect of the invention, the system further includes a template, where the template is suitable for overlaying the retrieved image for determining wear on the stationary side contact. The template may include a plurality of concentric arcs drawn at different scales for determining wear on a tip of the stationary side contact. According to yet another aspect of the invention, the first position may be below the at least one connector assembly and the second position may be above the at least one connector assembly. Alternatively, the first position may be above the at least one connector assembly and the second position may be below the at least one connector assembly.

According to another embodiment of the present invention, there is a method for on-site inspections of high-voltage circuit breakers. The method includes receiving a circuit breaker having a tank encapsulating at least one connector assembly, placing an X-ray unit at a first position exterior to the tank, placing a cassette having a digital imaging plate at a second position exterior to the tank, where the first and second positions lay on a plane that includes at least a portion of the at least one connector assembly, transmitting X-rays from the X-ray unit, where at least a portion of the X-rays traverses from the X-ray unit at the first position to the cassette at the second position, and retrieving an image from the digital imaging plate.

According to an aspect of the present invention, the method further includes disengaging at least one connector assembly such that the moving side contact and the stationary side contact are in a locked-out position. According to another aspect of the present invention, the cassette further includes one or more filtering screens. According to another aspect of the invention, the method further includes analyzing the image to determine a status of the circuit breaker, where analyzing the image includes enlarging the image on a computer. Analyzing the image may also include overlaying a template over the image to determine the extent of wear of at least a portion of the connector assembly. According to yet another aspect of the invention, the plane is perpendicular to at least a portion of the at least one connector assembly.

BRIEF DESCRIPTION OF THE DRAWINGS

Having thus described aspects of the invention in general terms, reference will now be made to the accompanying drawings, which are not necessarily drawn to scale, and wherein:

DETAILED DESCRIPTION OF THE INVENTION

The present invention now will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout.

Embodiments of the present invention are directed towards the use of radiography equipment, and in particular digital X-ray imaging equipment, for inspecting internal components of high-voltage circuit breakers. The use of digital X-ray imaging equipment allows digital images of these internal components to be obtained without moving or disassembling the circuit breakers. These X-ray images may then be digitally enhanced or manipulated as necessary in order to inspect the integrity of the internal components. The circuit breakers and the processes for utilizing the X-ray imaging equipment to inspect these circuit breakers will now be discussed below with reference to FIGS. 1-5.

High-voltage circuit breaker overview

Figure 1A:
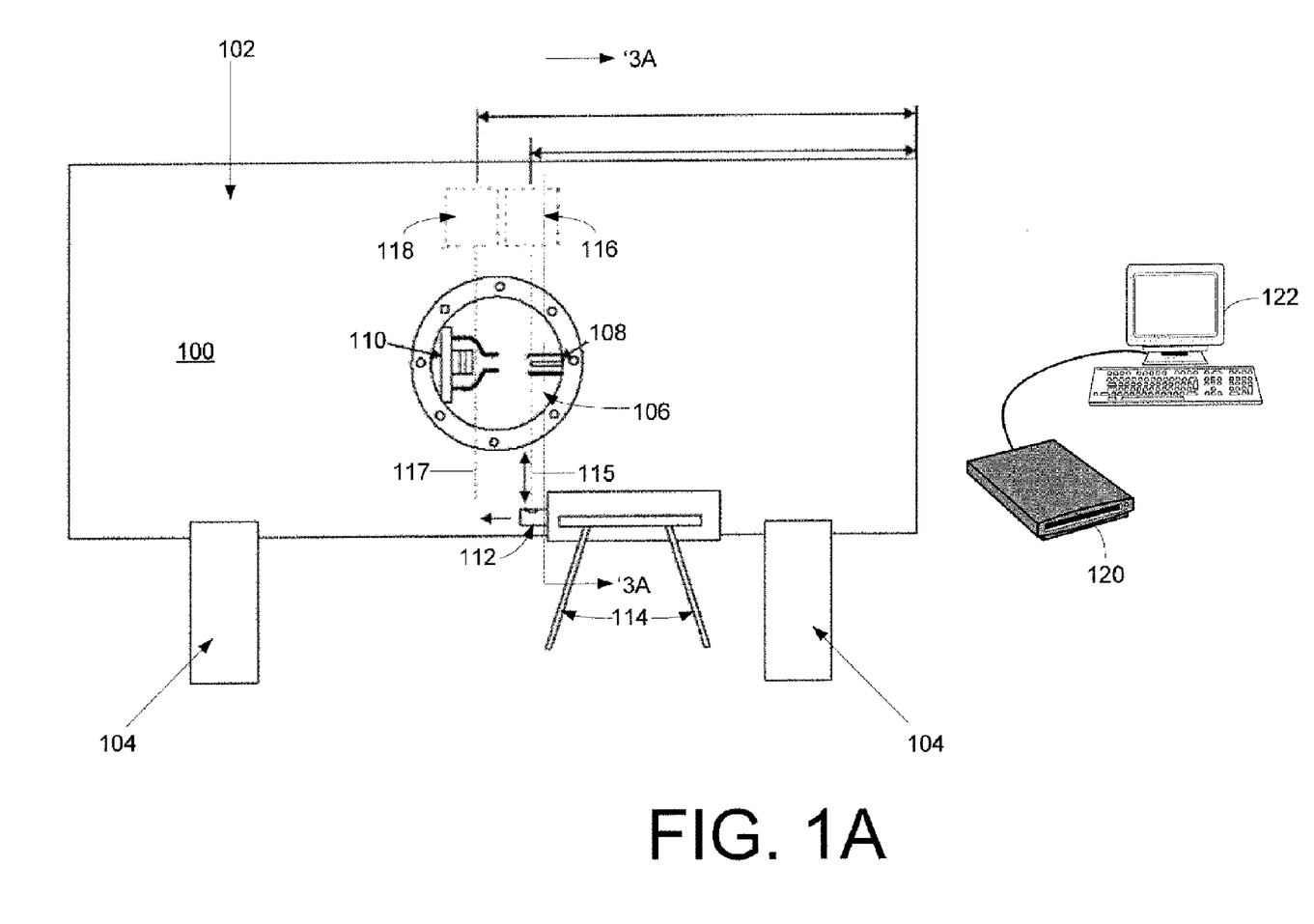
FIGS. 1A and 1B illustrate exemplary system overview diagrams in accordance with exemplary embodiments of the present invention.
Figure 1B:
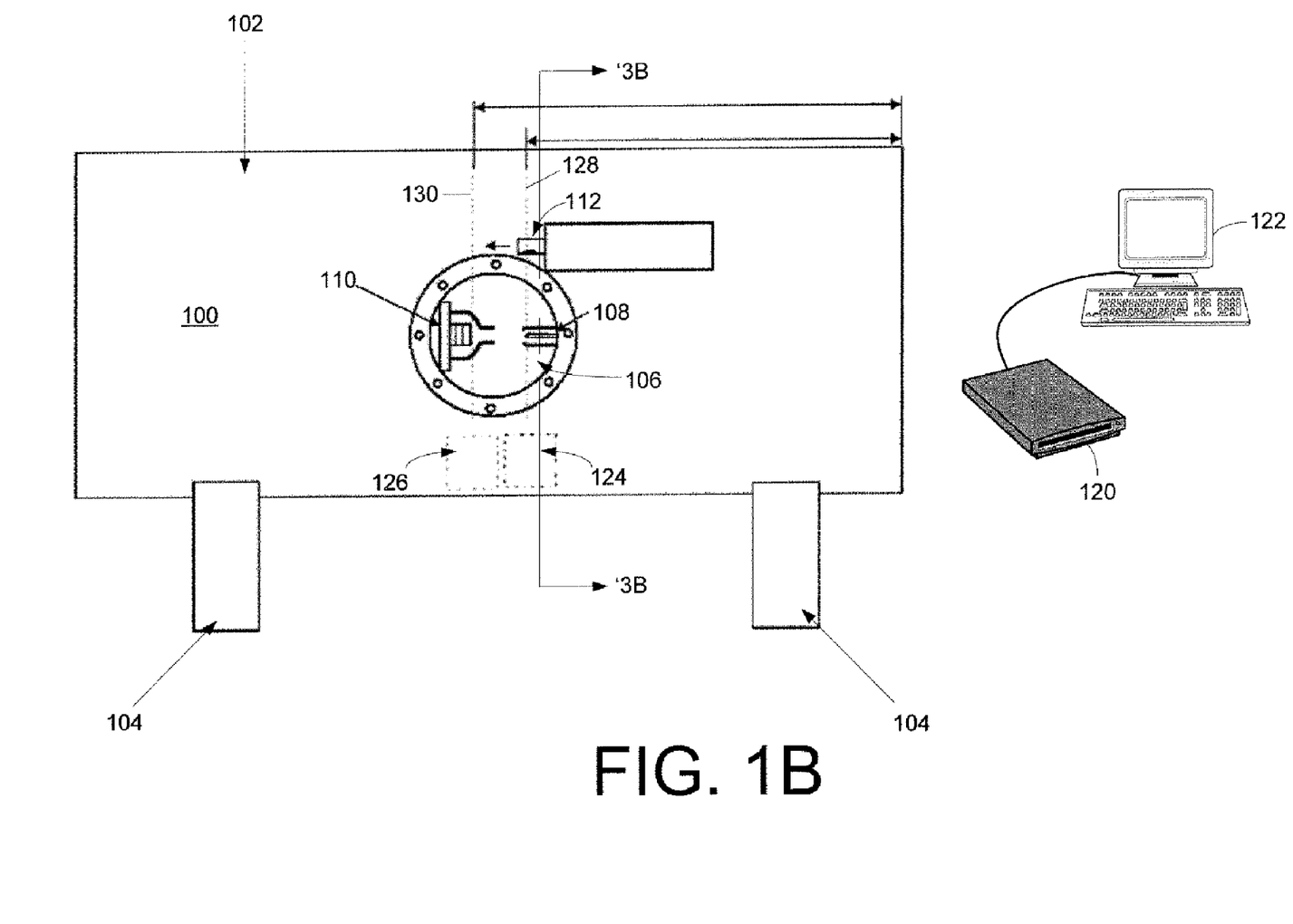

FIGS. 1A and 1B each illustrate an exemplary system overview of a high-voltage circuit breaker in accordance with embodiments of the present invention. In particular, FIGS. 1A and 1B show a high-voltage circuit breaker 100. The circuit breaker 100 may include an interrupter tank 102 that serves as the exterior housing for the circuit breaker 100. The interrupter tank 102 may vary in thickness and/or size depending on the desired operating specifications (e.g., voltage, amps, pressure, and the like) of the high-voltage circuit breaker 100. For example, the interrupter tank 102 may be 914.4 mm (i.e., 36 inches) in diameter with a thickness of 0.375 m for a 362-kV circuit breaker according to an exemplary embodiment. Interrupter tank 102 may be fabricated of steel, carbon steel, and other alloys and materials as known to one of ordinary skill in the art. The interrupter tank 102 may be physically stabilized during operation by one or more supports 104, which may be metal legs or stands according to an embodiment of the invention.

In addition, the circuit breaker 100 may include a man way or other inspection port 106. While inspection port 106 is shown as open in FIGS. 1A and 1B for illustrative purposes, it typically remains sealed during normal operation of the circuit breaker. According to an exemplary embodiment of the invention, the interrupter tank 102 may also contain gas, such as sulfur hexafluoride (SF6) gas or other insulating gas, to prevent internal arcing during operation of the circuit breaker 100.

As shown through the open inspection port 106 of FIGS. 1A and 1B, the circuit breaker 100 may include one or more contacts 108, 110 that form connector assemblies that comprise at least a portion of the internal components that may be inspected in accordance with an embodiment of the present invention. In particular, the circuit breaker 100 may include one or more stationary side contacts 108 (e.g., a male connector), each of which may be coupled to the corresponding one or more moving side contacts 110 (e.g., a female connector). According to an illustrative embodiment, there may be three sets of stationary side contacts 108 and moving side contacts 110. During normal operation of the circuit breaker 100, the stationary side contact 108 would be in communication with the moving side contact 110. However, when a fault is detected or when the circuit breaker is being inspected, the stationary side contact 108 and moving side contact 110 may be disengaged in a locked-out position as shown in FIGS. 1A and 1B.

Figure 2:
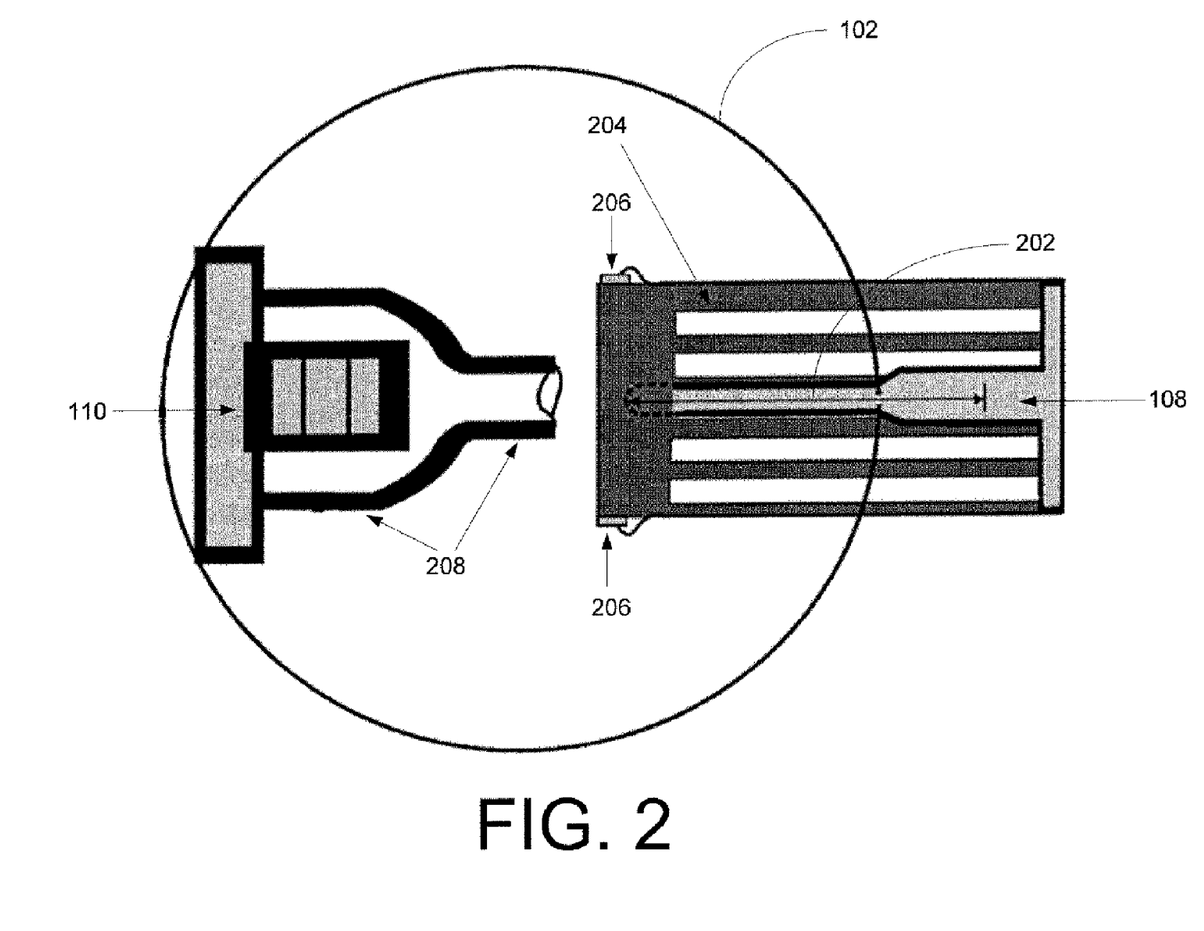
FIG. 2 illustrates an exemplary connector assembly in accordance with exemplary embodiments of the present invention.

FIG. 2 illustrates a more detailed view of the stationary side contact 108 and moving side contact 110 shown through the open inspection port 102 in FIGS. 1A and 1B. The stationary side contact 108 may be surrounded by the main contact 204, which may be known as the "bird cage." At an end of the main contact 204 are tungsten blocks 206. The area 202, which includes the shank and tip of the stationary side contact 108, may be one area of interest that may be inspected in accordance with embodiments of the present invention. In particular, the tip and/or shank in area 202 may indicate signs of wear that may require maintenance. Likewise, the moving side contact 110 may include a guide 208 for facilitating the connection between the moving side contact 110 with the stationary side contact 108. According to an embodiment of the invention, the guide 208 may be fabricated of Teflon. Like the stationary side contact 108, the moving side contact 110 may also be inspected for signs of wear that may require maintenance, according to exemplary embodiments of the present invention.

Radiography Imaging System

FIGS. 1A and 1B also disclose exemplary radiography equipment, and in particular X-ray equipment, for inspecting the internal components of the circuit breaker 100. In particular, an X-ray unit 112 may be utilized in conjunction with one or more digital imaging plates 116, 118, 124, 126 of FIGS. 1A and 1B to obtain images for one or more of the stationary side contacts 108 and moving side contacts 110. The X-ray unit 112 and corresponding digital imaging plates 116, 118, 124, or 126 may be placed in various positions around the interrupter tank 102 without departing from embodiments of the present invention.

According to an exemplary embodiment of the invention, one or more of the digital imaging plates 116, 118, 124, and 126 shown in FIGS. 1A and 1B may contain photosensitive storage phosphors that retain the latent image determined from the received X-ray energy from the X-ray unit 112. The digital imaging plates 116, 118, 124, 126 may be approximately 35 cm×43 cm (14"×17"), 35 cm×35 cm (14"×14"), according to an exemplary embodiment of the present invention. One of ordinary skill in the art will recognize that may other sizes of digital imaging plates are available and may be utilized as necessary.

Before positioning one or more of the digital imaging plates 116, 118, 124, 126 around the interrupter tank 102, one or more of the digital imaging plates 116, 118, 124, 126 may be placed in cassettes. According to an embodiment of the invention, the cassettes may be semi-rigid cassettes. Additionally, one or more screens may be placed in front of the digital imaging plates 116, 118, 124, 126 ("front screens") while one or more screens may be placed behind the digital imaging plates 116, 118, 124, 126 ("back screens") for filtering and/or intensifying the received X-ray energy from X-ray unit 112. The one or more front screens and back screens may be fabricated from metallic foil, lead, or other filtering or intensifying material. The front screen may filter out undesirable longer wavelengths while the back screen may prevent back scattering, thereby producing clearer images obtained from one or more of the digital imaging plates 116, 118, 124, 126. The front or back screens may vary in thickness, but may be 0.254 mm (i.e., 0.010 inches) according to an exemplary embodiment of the invention. One of ordinary skill in the art will recognize that other digital imaging plates may be utilized in accordance with embodiments of the invention, including those that utilize other compositions besides photosensitive storage phosphors.

Once one or more of the digital imaging plates 116, 118, 124, and 126 shown in FIGS. 1A and 1B have been exposed to the X-ray energy from X-ray unit 112 such that the desired latent image has been stored, the digital imaging plates 116, 118, 124, 126 may be processed by a scanner unit 120 to retrieve the latent image in digital form. According to one embodiment, the scanner unit 120 may be a General Electric (GE) CR100 desktop computed radiography scanner operating in conjunction with the Rhythm suite of software provided by GE Inspection Technologies. The scanner unit 120 may retrieve each latent image stored on digital imaging plates 116, 118, 124, 126 as a digital image viewable on computer 122. The scanner unit 120 may retrieve the latent image by scanning the digital imaging plates 116, 118, 124, 126 with one or more laser beams. The laser beam may cause the latent image stored in the photosensitive storage phosphors in the digital imaging plates 116, 118, 124, 126 to be released as visible light. The visible light can then be captured by the scanner unit 120 and converted into a digital bit scream that encodes the digital image for the computer 122 according to an embodiment of the invention.

The digital image can then be modified or manipulated via the computer 122. For example, one or more filtering algorithms may be performed on the digital image to enhance the image. The digital image can also be enlarged to view the area of interest. Many other modifications or manipulations can be performed on the digital image as known to one of ordinary skill in the art. In addition or in the alternative, the digital image may also be printed, perhaps as a photograph, in exemplary embodiments of the present invention.

Exemplary Inspection Process

1. Positioning

In accordance with an exemplary embodiment of the present invention, the X-ray unit 112 may be generally positioned under the stationary side contacts 108 and moving side contacts 110 around the interrupter tank 102 as shown in FIG. 1A. If the X-ray unit 112 were positioned as shown in FIG. 1A, then the digital imaging plates 116, 118 may generally be placed generally above the stationary side contacts 108 and moving side contacts 110. According to an aspect of the invention, the X-ray unit 112 and the digital imaging plates 116,118 may be separated by less than 180 degrees around the interrupter tank 102 where the stationary side contacts 108 and moving side contacts 110 are not centered in the interrupter tank 102. Alternatively, according to another aspect of the invention, the X-ray unit 112 and the digital imaging plates 116,118 may be separated by about 180 degrees around the interrupter tank 102. The X-rays originating from the X-ray unit 112 may be captured and/or recorded by one or more corresponding digital imaging plates 116, 118. For example, when inspecting stationary side contact 108, X-ray unit or unit 112 may be positioned in an approximately perpendicular plane 115 that includes the desired portion of the stationary side contact 108, where the emitted X-rays from the X-ray unit or unit 112 are recorded on digital imaging plate 116. Similarly, the approximately perpendicular plane 117 may be utilized when inspecting the moving side contact 110.

Figure 3A:
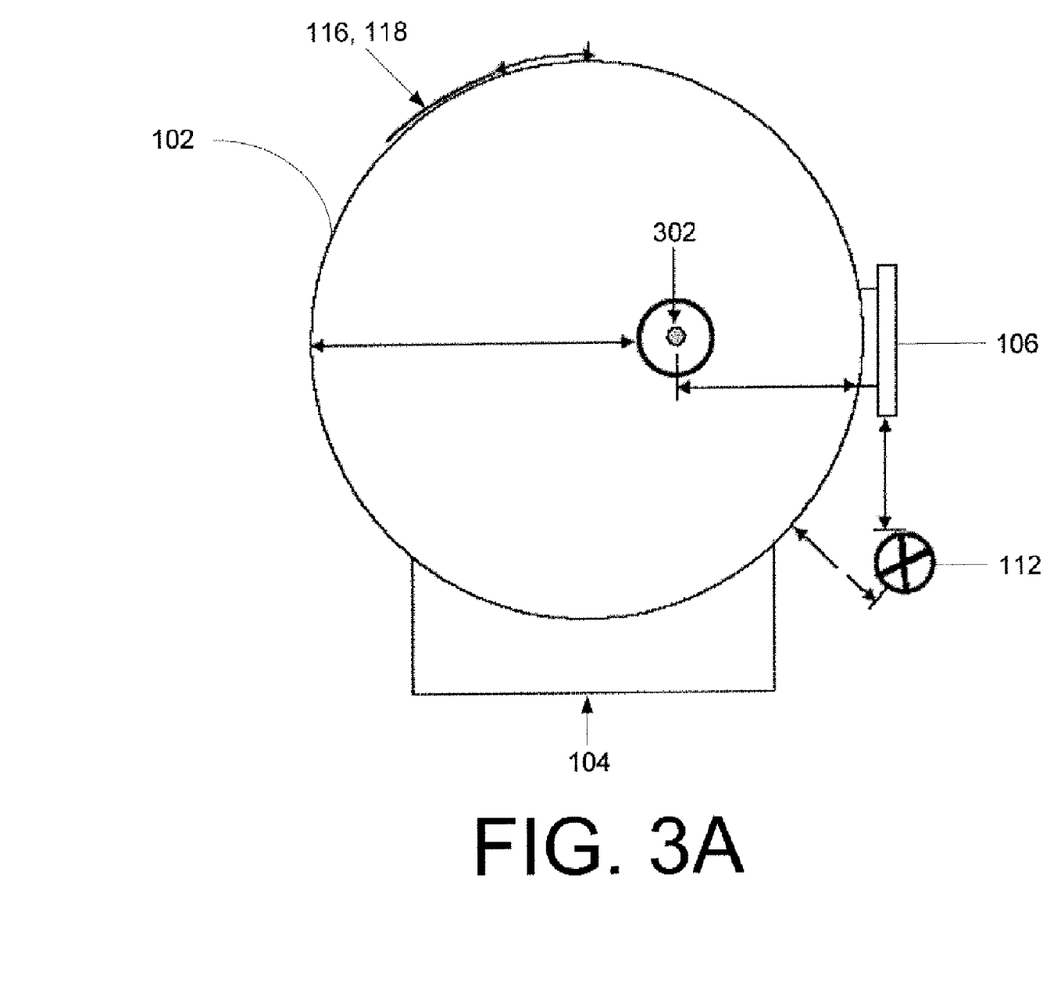
FIG. 3A illustrates a cross-sectional view of the X-ray unit, digital imaging plates, and circuit breaker in FIG. 1A in accordance with an embodiment of the present invention.

FIG. 3A shows a cross-sectional view of the X-ray unit 112, digital imaging plates 116, 118, and circuit breaker 100 taken along line '3A-'3A in FIG. 1A. As shown in FIG. 3A, the connector assembly 302 which include the stationary side contact 108 and the moving side contact 110 may not necessarily be centered in the interrupter tank 102. The X-ray unit 112 will then be generally placed below the connector assembly 302 while the digital imaging plate 116 or 118 will generally be placed above the connector assembly 302. A perpendicular shot will then be taken by the X-ray unit such that the shot is substantially perpendicular to the stationary side contact 108 or the moving side contact 110. In accordance with an embodiment of the present invention, one or more perpendicular shots will be taken for each stationary side contact 108 and moving side contact 110 that is to be inspected. Because the tip of the stationary side contact 108 may be obscured by the tungsten blocks 206 shown in FIG. 2, the X-ray unit 112 and corresponding digital imaging plate 116 or 118 may be positioned such that the perpendicular shot does not block a view of the tip of the stationary side contact 108.

Likewise, in an alternative embodiment of the present invention, as shown in FIG. 1B, the X-ray unit 112 may instead be generally positioned above the stationary side contacts 108 and moving side contacts 110 around the interrupter tank 102. As shown in FIG. 1B, the corresponding digital imaging plates 124, 126 may then be generally positioned below the stationary side contacts 108 and moving side contacts 110. According to an aspect of the invention, the X-ray unit 112 and the digital imaging plates 124, 126 may be separated by less than 180 degrees around the interrupter tank 102 where the stationary side contacts 108 and moving side contacts 110 are not centered in the interrupter tank 102. Alternatively, according to another aspect of the invention, the X-ray unit 112 and the digital imaging plates 124, 126 may be separated by about 180 degrees around the interrupter tank 102. For example, the X-ray unit 112 may be positioned in an approximately perpendicular plane 130 that includes the desired portion of the moving side contact 110, where the emitted X-ray energy from the X-ray unit 112 is captured and/or recorded on digital imaging plate 124. Similarly, the approximately perpendicular plane 128 may be utilized when inspecting the stationary side contact 108.

Figure 3B:
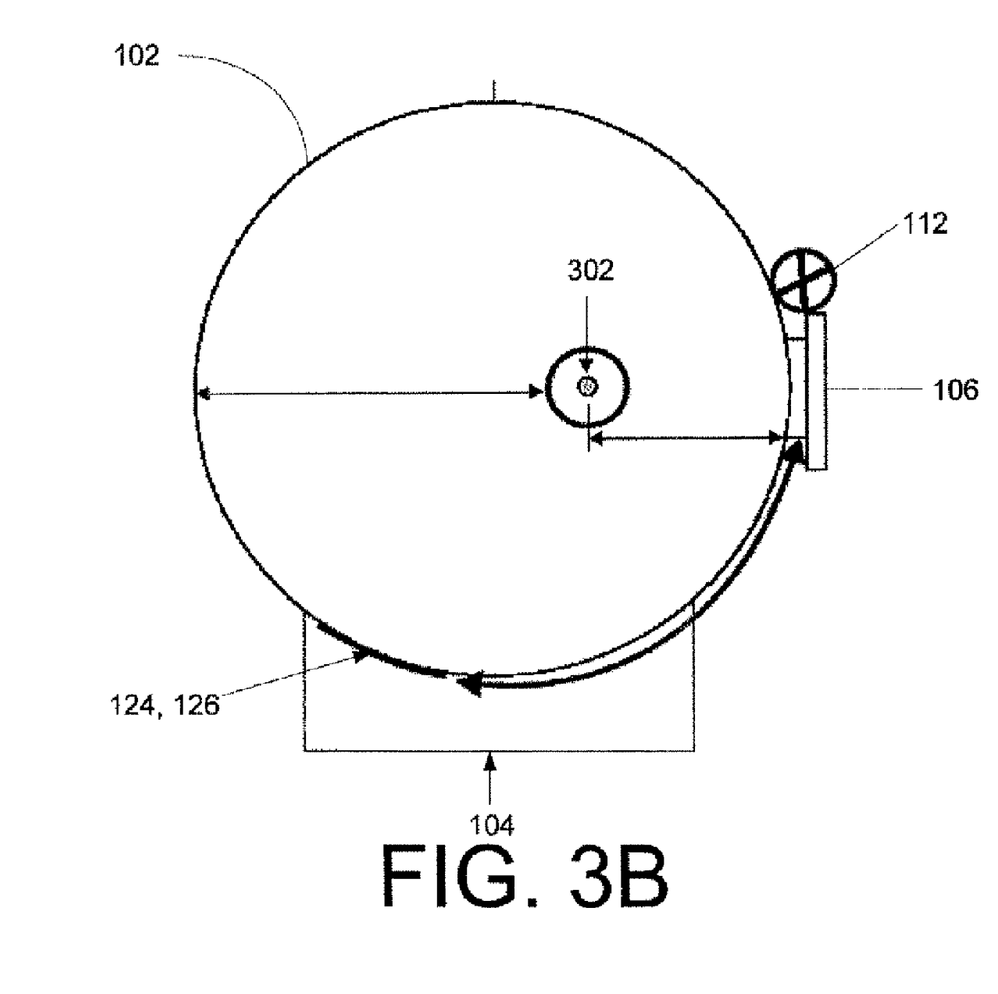
FIG. 3B illustrates a cross-sectional view of the X-ray unit, digital imaging plates, and circuit breaker in FIG. 1B in accordance with an embodiment of the present invention.

FIG. 3B shows a cross-sectional view of the X-ray unit 112, digital imaging plates 124, 126, and circuit breaker 100 taken along line '3B-'3B shown in FIG. 1B. The X-ray unit 112 will then be generally placed above the connector assembly 302 while the digital imaging plate 124 or 126 will generally be placed above the connector assembly 302. A perpendicular shot will then be taken by the X-ray unit such that the shot is substantially perpendicular to the stationary side contact 108 or the moving side contact 110. Again, one or more perpendicular shots will be taken for each stationary side contact 108 and moving side contact 110 that is to be inspected. Because the tip of the stationary side contact 108 may be obscured by the tungsten blocks 206 shown in FIG. 2, the X-ray unit 112 and corresponding digital imaging plate 116 or 118 may be positioned such that the perpendicular shot does not block a view of the tip of the stationary side contact 108.

One of ordinary skill in the art will recognize that other variations in the positioning of the X-ray unit 112 and digital imaging plates for the image shots are possible. For example, the X-ray unit and the corresponding digital imaging plates may be positioned on a horizontal plane covering one or more of the stationary side contacts or moving side contacts. Where necessary, a stand 114, crane, or other elevating means may be utilized to placed the X-ray unit 112 in the desired position according to an exemplary embodiment of the present invention.

While the above-described process discloses inspecting the stationary side contacts 108 and/or moving side contacts 110, one of ordinary skill in the art will readily recognize that other inspections for circuit breaker 100 may be performed. For example, the interrupter tank 102 of circuit breaker 100 may be inspected using the above-described process for the detection of foreign objects.

2. Radiography Equipment Operating Parameters

Figure 4A:
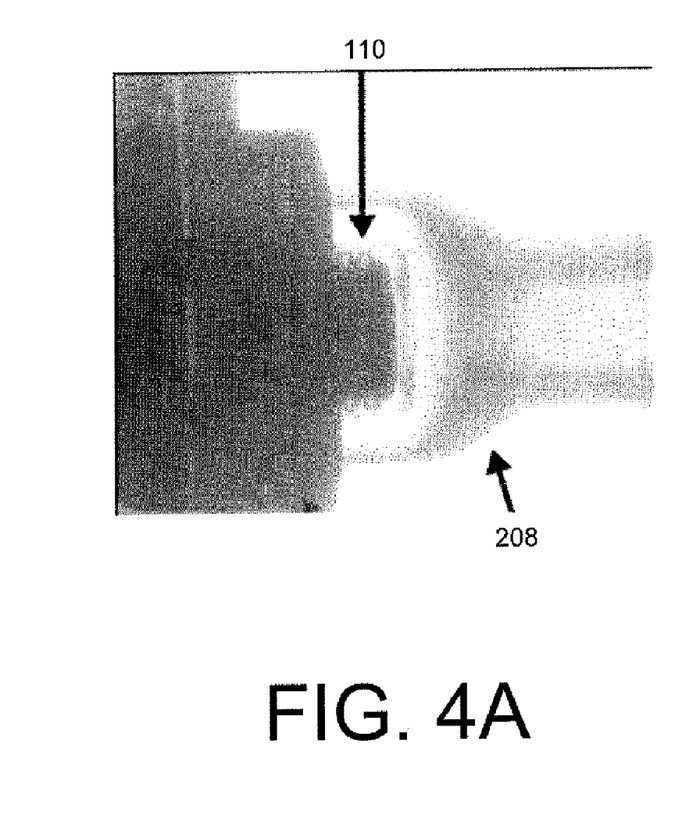
FIGS. 4A and 4B illustrate digital X-ray images obtained during the inspection process in accordance with embodiments of the present invention.
Figure 4B:
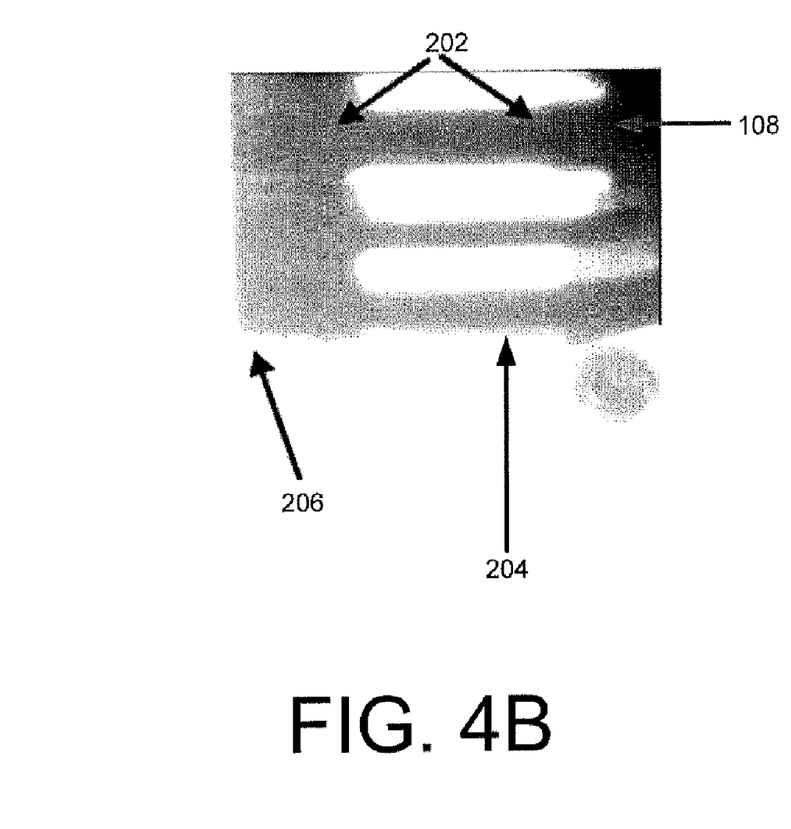

According to one embodiment of the invention, the operating parameters (e.g., intensity, time, and film to focal distance (FFD), etc.) of the X-ray energy from X-ray unit 112 to one or more digital imaging plates 116, 118, 124, 126 may vary depending at least in part on the size (e.g., diameter, thickness, etc.) of the interrupter tank 102 of the circuit breaker 100, and the density of the component to be inspected (e.g., male connector, female connector, etc.). As an example, for a carbon steel interrupter tank 102 with a 914.4 mm (i.e., 36 inches) diameter and a thickness of 0.375 m, the exposure of one or more of digital imaging plates 116, 118, 124, 126 from X-ray unit 112 may be generally between approximately 200 KV-300 KV at approximately 14-22 milliamp minutes (MAM), or more specifically between approximately 240 KV-270 KV at approximately 15-21 MAM. In particular, when the stationary side contact 108 is being inspected, the X-ray unit 112 may emit X-ray energy at approximately 240 KV for approximately 15 MAM according to an exemplary embodiment. On the other hand, when the moving side contact 110 is being inspected, the X-ray unit 112 may emit X-ray energy at approximately 240 KV for approximately 15 MAM according to an exemplary embodiment. In addition, the FFD, which may depend at least in part on the size of the interrupter tank 102, may be approximately 152 cm (e.g., 60 inches) in the exemplary embodiment. Many other variations will be well-known to one of ordinary skill in the art 3. Analysis of Digital Images FIGS. 4A and 4B disclose exemplary digital images obtained in accordance with embodiments of the present invention. In particular, FIG. 4A shows a digital X-ray image of the moving side contact 110 and FIG. 4B shows a digital X-ray image of the stationary side contact 108. The digital images can also be modified, manipulated, enhanced, and/or printed via the computer 122 as necessary. The digital images shown in FIGS. 4A and 4B may be analyzed to determine if any maintenance needs to be performed on the moving side contact 110 and/or the stationary side contact 108. In particular, FIG. 4A may be examined to determine deformation of the moving side contact 110 along with pitting on the Teflon guide 208. With respect to the stationary side contact 108, the shank and tip shown in area 202 may be examined for wear and "arc striking."

Figure 5:
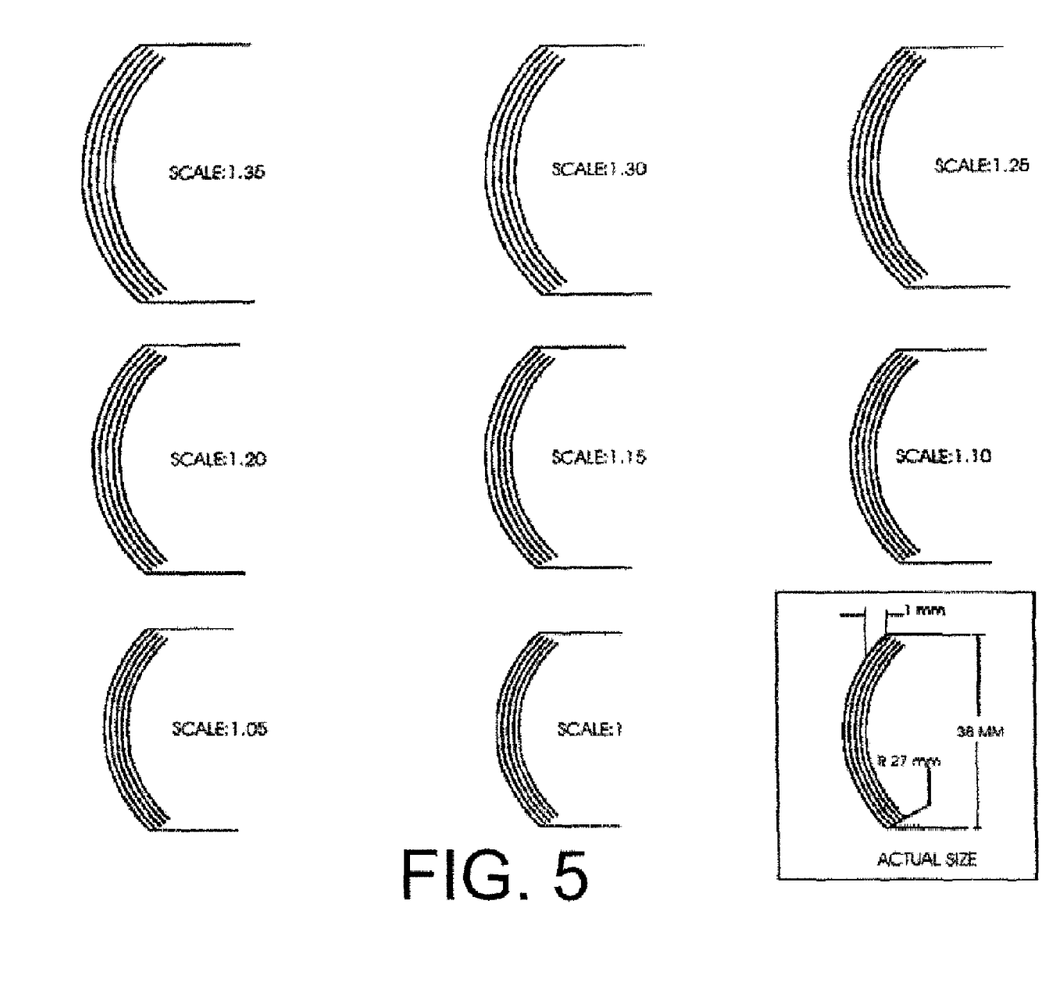
FIG. 5 illustrates templates utilized to analyzing digital X-ray images in accordance with embodiments of the present invention.

In accordance with exemplary embodiments of the present invention, templates may also be utilized to determine the extent of wear on the tip of the stationary side contact 108. Referring to FIG. 5, the image of the tip of the stationary side contact 108 may be compared to the templates shown in FIG. 5. The templates in FIG. 5 show scaled versions of outlines of stationary side contacts 108. In an exemplary embodiment of the present invention, there templates may be scaled from an actual size to about 35% larger than actual size as shown in FIG. 5. One of ordinary skill in the art will recognize that many other scalings can be utilized. Each of these templates shows concentric arc patterns that can be used to determine the extent of wear on the tip of the stationary side contact 108. More specifically the image of the tip of the stationary side contact 108 can be aligned to the appropriate template shown in FIG. 5, and the concentric arcs allows a determination to be as to the amount of wear (e.g., distance between concentric arcs=1 mm) on the tip.

According to one embodiment of the present invention, the template shown in FIG. 5 can be printed on a transparency. The transparency can then be overlaid over an image of the tip of the stationary side contact 108. The correctly-scaled template on the transparency will be placed over the image of the tip of the stationary side contact 108. The concentric arcs on the correctly-scaled template will then be utilized to determine the extent of wear on the tip of the stationary side contact 108.

In accordance with another embodiment of the present invention, a computer algorithm on computer 122 may digitally determine the extent of wear on the digital image of the stationary side contact 108. In one embodiment, the computer 122 may receive a digital image of the tip of the stationary side contact 108. The computer algorithm may apply digitally-stored templates over the digital image of the tip in order to determine the correct scaling. The computer algorithm will then determine the difference between the expected tip curvature and the actual tip curvature for determining wear on the tip. Many other variations of the computer algorithm will be readily recognized by one of ordinary skill in the art.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. A method for non-intrusively inspecting circuit breakers, comprising:
   receiving at least one circuit breaker, wherein the circuit breaker comprises a tank having an interior with one or more connector assemblies;

placing an X-ray unit at a first location of an exterior of the tank;

placing at least one digital imaging plate at a second location of the exterior the tank;

generating X-rays from the X-ray unit, such that at least a portion of the generated X-rays traverse a plane that includes at least a portion of the one or more connector assemblies and at least a portion of the at least one digital imaging plate;

retrieving an image from each digital imaging plate, wherein each image includes at least a portion of the one or more connector assemblies; and determining an extent of wear of the one or more connector assemblies by determining a scaling associated with the image.

2. The method of claim 1, wherein the connector assembly includes one or both of a stationary side contact and a moving side contact.

3. The method of claim 2, wherein determining the extent of wear of the one or more connector assemblies includes determining the extent of wear of the stationary side contact.

4. The method of claim 1, wherein determining the scaling includes determining a scale for a template, wherein the scaled template is compared to the image to determine the extent of wear of the one or more connector assemblies.

5. The method of claim 1, wherein retrieving an image comprises retrieving an image from each digital imaging plate via at least one scanner unit operable with the digital imaging plate.

6. The method of claim 1, wherein the image can be directly manipulated on a computer.

7. A system for non-intrusive inspections of circuit breakers, comprising:

a circuit breaker having at least one connector assembly;

an X-ray unit at a first position of the circuit breaker for transmitting X-ray energy, wherein the transmitted X-ray energy is directed towards at least a portion of the at least one connector assembly;

a digital imaging plate at a second position of the circuit breaker substantially opposite the first position for receiving the transmitted X-ray energy, wherein the digital imaging plate stores an image that is defined, at least in part, by the received X-ray energy; and a computer for receiving the stored image, wherein the computer is operative to determine an extent of wear of the at least one connector assembly by determining a scaling associated with the image.

8. The system of claim 7, wherein the computer receives the stored image via a scanner unit that retrieves the stored image from the digital imaging plate.

9. The system of claim 7, wherein the stored image captures at least a portion of the at least one connector assembly.

10. The system of claim 9, wherein the portion of the at least one connector assembly includes a stationary side contact.

11. The system of claim 7, wherein determining the scaling includes determining a scale for a template, wherein the scaled template is compared to the image to determine the extent of wear of the at least one connector assembly.

12. The system of claim 11, wherein the template includes a plurality of concentric arcs drawn at different scales for determining the extent of wear of the at least one connector assembly.

13. The system of claim 8, wherein the first position is below the at least one connector assembly and the second position is above the at least one connector assembly.

14. The system of claim 8, wherein the first position is above the at least one connector assembly and the second position is below the at least one connector assembly.

15. A method for on-site inspections of high-voltage circuit breakers, comprising:

receiving a circuit breaker having a tank encapsulating at least one connector assembly;

placing an X-ray unit at a first position exterior to the tank;

placing a cassette having a digital imaging plate at a second position exterior to the tank, wherein the first and second positions lay on a plane that includes at least a portion of the at least one connector assembly;

transmitting X-rays from the X-ray unit, wherein at least a portion of the X-rays traverses from the X-ray unit at the first position to the cassette at the second position;

retrieving an image from the digital imaging plate; and determining an extent of wear of the at least one connector assembly by determining a scaling associated with the image.

16. The method of claim 15, further comprising disengaging at least one connector assembly such that the moving side contact and the stationary side contact are in a locked-out position.

17. The method of claim 15, wherein the cassette further includes one or more filtering screens.

18. The method of claim 15, wherein determining the extent of wear of the at least one connector assembly includes enlarging the image on a computer.

19. The method of claim 15, wherein determining the scaling includes determining a scale for a template, wherein the scaled template is compared to the image to determine the extent of wear of the at least one connector assembly.

20. The method of claim 15, wherein the plane is perpendicular to at least a portion of the at least one connector assembly.

* * * * *